United States Patent
Coffin

(10) Patent No.: US 6,410,527 B1
(45) Date of Patent: Jun. 25, 2002

(54) METHOD OF TREATING OBSESSIVE COMPULSIVE DISORDERS, SOMATOFORM DISORDERS, DISSOCIATIVE DISORDERS, EATING DISORDERS, IMPULSE CONTROL DISORDERS, AND AUTISM

(75) Inventor: Vicki L. Coffin, Basking Ridge, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/259,719

(22) Filed: Mar. 1, 1999

Related U.S. Application Data
(60) Provisional application No. 60/076,471, filed on Mar. 2, 1998.

(51) Int. Cl.$^7$ .................... A61K 31/55; A61K 312/395; A61K 31/445; C07D 223/14; C07D 491/04
(52) U.S. Cl. ........................................ 514/217; 514/215
(58) Field of Search .................... 514/215, 217

(56) References Cited

U.S. PATENT DOCUMENTS

| | | | |
|---|---|---|---|
| 4,973,586 A | 11/1990 | Berger et al. ........... | 514/217 |
| 5,258,378 A | * 11/1993 | Clark et al. | |
| 5,302,716 A | * 4/1994 | Berger | |
| 5,605,897 A | 2/1997 | Beasley, Jr. et al. ...... | 514/220 |
| 5,741,789 A | 4/1998 | Hibschman et al. | |

FOREIGN PATENT DOCUMENTS

| | | | |
|---|---|---|---|
| WO | 93 13073 | * | 7/1993 |
| WO | 93 1702 | * | 9/1993 |
| WO | 95 25102 | * | 9/1995 |
| WO | 99 21540 A2 A3 | * | 5/1999 |
| WO | 9944615 A1 | * | 9/1999 |

OTHER PUBLICATIONS

Iorio Et Al J. Pharmacol. Exp. Ther. 258(1):118–123 SCH 23390 Potential SCH 39166 Antipsychotic, (1991).*
Tedford Et Al Pschychopharmacology 113(2): 199–204 SCH 39166 Cond. Avoiding Behavior, (1993).*
Tedford Et Al Drug Res. Dev. 26(4):389–403 SCH 39166 Cond. Avoid. Behavior, (1992).*
Coffin Et Al J Neurochem. 57(6):2001–2010 SCH 39166 Antipsychotic, (1992).*
McQuade Et Al Eur. J. Pharmacol. 215(1): 29–34 SCH 39166 Antipsychotic, (1992).*
Coffin Et Al J. Neuro Chem. 57(6):2001–2010 SCH 39166 SCH170 Phroma, (1991).*
Chipkin Et Al J. Pharmacol. Exp Ther. 247(3):1093–1102 SCH 39166 Antipsychotic, (1988).*
J. Med. Chem. 38(21):4284–4293, (1995).*
Gilbert Et Al Brain Res. Bull. 15(4): 385–389 SCH 23390 Reversed Anorexia, 1988.*
Arnt Et Al Evr. J. Pharmacol. 133(2):137–145 SCH 23390 Blocks Sterotyped Behavior, 1987.*
Delbs Et Al Neuroscience (Oxford) 39(1) : 59–67 SCH 23390 Antagonizes Stereotype Behavior, 1990.*
Bruhwyler Et Al Pharmacol Biochem. Behav. 39(2) : 367–371 SCH 23390 Anxiolytic Against Anxiety, 1991.*
Blaumonde Et Al Evr. J. Pharmacol. 216(2):157–165 SCH 23390 Antidepressant Forced of Swim Test, 1992.*
Simon Et Al Pharmacol. Biochem. Behav 45(3): 685–690 SCH 23390 Antagonize Anxiety, 1993.*
Rodgers Et Al Pharmacol. Biochem. Behav. 49(4); 985–995 SCH 23390 Anxiety Effect., 1994.*
Harrison Et Al Psychopharmacology 133(4):329–342 SCH 23390 Blocks Impulse Behavior, 1997.*
Woodskettelburger Et Al Exp. Opinion. Invest. Drugs 6(10):1369–1381 SCH 23390 Obsessive Compulsive, 1997.*
Yeghiayian Et Al Pharma Cology Biochemistry Behav. 5(2/3):493–501 SCH 23390 Obsession, 1995.*
Hart Braves Et Al Psychopharmacology 90(3):355–367 SCH 23390 Compuls. Behav. Blocked, 1986.*
Balthazart Et Al Physiol. & Behav. 62(3);571–580 SCH 23390 Male Sexual Behavior Appetitive & Consummate Block, 1997.*
Zarrindast Et Al Evr. J. Pharmacol. 321(21):157–162 SCH 23390 Anoroxia Induced., 1993.*
Rowlott Et Al Synadse 14(2):160–168 SCH 23390 Behavior Senstise, 1993.*
Zarrindast Et Al Gen. Pharmacol. 22(6): 1011–1016 SCH 23390 Induces Anorexia, 1991.*
Chemical Abstracts, AN=130:46933.XP002107374, Peacock et al., "D–1 Antagonists in Animal Models and in Schizophrenia: Potential Antipsychotic Effects and Extrapyramidal Side Effects."
Balthazart et al., "Differential Effects of D1 and D2 Dopamine–Receptor Agonists and Antagonists on Appetitive and Consumatory Aspects of Male Sexual Behavior in Japanese Quail"—*Physiol. Behav.*, 62: Issue 3, 571–589, 1997.
Acri, J.B., et al., Behavioral Effects and Dopamine Antagonists Properties of N–Alkylaminobenzazepines, *Drug Development Research*, 37: 39–47, 1996.
Hollander, Eric, et al., New Frontiers in OCD Spectrum Research for Psychiatry and Primary Care, *The Journal of Clinical Psychiatry*, 57: 3–87, 1996.
Shah, Jamshed H., et al., (±)–(N–Alkylamino) benzazepine Analogs: Novel Dopamine $D_1$ Receptor Antagonists, *J. Med., Chem.*, 38: 4284–4293, 1995.

(List continued on next page.)

Primary Examiner—Shep K. Rose
(74) Attorney, Agent, or Firm—William Y. Lee; Arthur Mann

(57) ABSTRACT

A method for treating obsessive-compulsive disorders, somatoform disorders, dissociative disorders, eating disorders, impulse control disorders, and autism is disclosed. These disorders are treated by administering an effective amount of a D1/D5 antagonist.

8 Claims, No Drawings

OTHER PUBLICATIONS

Gnanalingham, Kanna K., et al., Selective dopamine antagonist pretreatment on the antiparkinsonian effects of benzazepine $D_1$ dopamine agonists in rodent and primate models of Parkinson's disease—the differential effects of $D_1$ dopamine antagonists in the primate, *Psychopharmacology*, 117: 403–412, 1995.

Cook, Edwin H., Jr., et al., Receptor Inhibition by Immunoglobulins: Specific Inhibition by Autistic Children, Their Relatives, and Control Subjects, *Journal of Autism and Developmental Disorders*, 23: No. 1, 1993.

Coffin, Vicki L., et al., SCH 39166, A Potential Antipsychotic Drug, Does Not Evoke Movement Disorders in Cebus Monkeys, *Neurochem. Int.*, 20: 141S–145S, 1992.

Criswell, Hugh E., et al., Pharmacologic Evaluation of SCH–39166, A–69024, NO–0756, and SCH–23390 in Neonatal–6–OHDA–Lesioned Rats, *Neuropsychopharmacology*, 7: No. 2, 95–102, 1992.

McHugh, Daniel and Vicki Coffin, The reversal of extrapyramidal side effects with SCH 39166, a dopamine $D_1$ receptor antagonist, *European Journal of Pharmacology*, 202: 133–134, 1991.

Eric Hollander, M.D., *Obsessive–Compulsive–Related Disorders*, 1–17.

Kerkman, Daniel J., et al., A–69024: a non–benzazepine antagonists with selectivity for the dopamine D–1 receptor, *European Journal of Pharmacology*, 166: 481–491, 1989.

John L. Waddington, Therapeutic Potential of Selective D–1 Dopamine Receptor Agonists and Antagonists in Psychiatry and Neurology, *Gen. Pharmac.*, 19:, No. 1, 55–60, 1988.

Michèle Beaulieu, Clinical Importance of D–1 and D–2 Receptors, *The Canadian Journal of Neurological Sciences*, 14: 402–406, 1987.

Gilbert et al., "Analysis of Dopamine D1 and D2 Receptor Involvement in D–and 1–Amphetamine–Induced Anorexia in Rats", *Brain Res. Bull.*, 15:, Issue 4, 385–398, 1985.

\* cited by examiner

METHOD OF TREATING OBSESSIVE COMPULSIVE DISORDERS, SOMATOFORM DISORDERS, DISSOCIATIVE DISORDERS, EATING DISORDERS, IMPULSE CONTROL DISORDERS, AND AUTISM

This application claims the benefit of U.S. Provisional Application No. 60/076,471, filed Mar. 2, 1998.

BACKGROUND OF THE INVENTION

This invention is directed to the treatment of a group of disorders marked by repetitive, intrusive thoughts and/or ritualistic behaviors, i.e., obsessive-compulsive disorder, somatoform disorders, dissociative disorders, eating disorders, impulse control disorders, and autism.

Obsessive-compulsive disorder ("OCD"), recognized to be among the most common of all psychiatric disorders, occurs in 2 to 3% of the U.S. population. OCD is characterized by anxiety-provoking and intrusive thoughts (e.g., fear of contamination and germs, doubt and uncertainty about future harm, need for symmetry, etc.) which lead to ritualistic and/or irrational behavior (e.g., constant checking, washing, touching, counting, etc.). See Hollander, et al., J. Clin Psychiatry 57 (Suppl. 8), pp. 3–6 (1996).

Somatoform disorders (e.g., body dysmorphic disorder and hypochondriasis) are characterized by abnormal preoccupation with one's appearance or physical condition. For example, body dysmorphic disorder is a preoccupation with an imagined or slight defect in appearance. Many sufferers of body dysmorphic disorder are severely debilitated by their abnormal preoccupation, with significant impairment in social, occupational, or other important aspects of daily life. See Phillips, J. Clin Psychiatry 57 (suppl. 8), pp. 61–64 (1996). Hypocondriasis is characterized by a persistent conviction that one is, or is likely to become ill. Many hypochondriacs are unable to work or engage in ordinary activities due to their preoccupation with illness.

Dissociative disorders (e.g., depersonalization) are characterized by sudden temporary alterations in identity, memory, or consciousness, segregating normally integrated memories or parts of the personality from the dominant identity of the individual. Depersonalization disorder, which is a dissociative disorder, is characterized by one or more episodes of depersonalization (feelings of unreality and strangeness in one's perception of the self or one's body image).

Eating disorders (e.g., anorexia nervosa, bulimia, and binge eating) are characterized by abnormal compulsions to avoid eating or uncontrollable impulses to consume abnormally large amounts of food. These disorders affect not only the social well-being, but the physical well-being of sufferers.

Impulse control disorders (e.g., pathological gambling, compulsive buying, sexual compulsions and kleptomania) are characterized by a preoccupation with, and an inability to refrain from repeatedly engaging in various behaviors that are either socially unacceptable, or abnormally excessive by societal norms.

Autism is a disorder characterized by a preoccupation with one's own self and a severe impairment of the ability to perceive or react to outside stimuli in a normal fashion. Many autistics are incapable of even communicating with others.

In view of the tragic and debilitating effects of these disorders, there is a strong need for a drug therapy which can effectively treat such disorders.

There have been some reports that certain D1 antagonists: inhibit L-DOPA-induced self-mutilatory behavior in neonatal-6-hydroxypropamine lesioned rats; are able to block amphetamine-induced locomotor activity and apomorphine-induced stereotypy in rats; inhibit grooming and oral activities induced by the administration of D1 agonists to marmosets; inhibit apomorphine induced stereotypy in mice; and reverse extrapyramidal side effects in monkeys treated with haloperidol. See Criswell, et al., Neuropsychopharmacology, 7 (2) pp. 95–103 (1992); Kerkman, et al., European Journal of Pharmacology, 166 (3) 481–91 (1989); Gnanalingham, et al., Psychophamacology, 117 (4), pp. 403–12 (1995); Acri, et al., Drug Dev. Res. 37 (1), pp. 39–47 (1996); McHugh, et al., European Journal of Pharmacology 202, pp. 133–134 (1991); Coffin, et al., Neurochem. Int., Vol. 20, Suppl., pp. 141S–145S (1992); Waddington, Gen. Pharmac. Vol. 19, No. 1, pp. 55–60 (1988); and Beaulieu, Can. J. Neurol. Sci., 14: 402–406 (1987).

SUMMARY OF THE INVENTION

The present invention provides a method for treating a human suffering from obsessive compulsive disorder, a somatoform disorder, a dissociative disorder, an eating disorder, an impulse control disorder, or autism by administering an effective amount of a D1/D5 antagonist.

DETAILED DESCRIPTION OF THE INVENTION

As used herein, the following terms have the meanings set forth below.

"D1/D5 antagonist" is a compound that selectively binds to the D1 receptors and/or the D5 receptors in the brain, thereby decreasing or preventing dopamine access to these sites. A compound "selectively binds" to the D1 and/or D5 receptors when it exhibits greater binding to either the D1 or D5 receptors than it does to the D2 receptors. D1/D5 antagonists include compounds that bind only to the D1 receptor (pure D1 antagonists), only to the D5 receptor (D5 antagonists), as well as compounds that bind to both the D1 and D5 receptors.

Non-limitative examples of D1/D5 antagonists include: SCH 39166 [(−)-trans-6,7,7a, 8,9,13b-hexahydro-3-chloro-2-hydroxy-N-methyl-5-H-benzo[d]naphtho{2,1-b}azepine HCl]; SCH23390 [(R)-(+)-8-chloro-2,3,4,5-tetrahydro-3-methyl-5-phenyl-1H-3-benzazepin-7-ol maleate]; BTS-73-947 [(S)-1-(1 -(2-chlorophenyl)cyclopropyl)-7-hydroxy-6-methoxy-2-methyl-1,2,3,4-tetrahydroisoquinoline]; A-69024 [1-(2-bromo-4,5-dimethoxybenzyl)-7-hydroxy-6-methoxy-2-methyl-1,2,3,4-tetrahydroisoquinoline]; JHS-271 [8-chloro-3-[6-(dimethylamino)hexyl]-2,3,4,5-tetrahydro-5-phenyl-1H-3-Benzazepin-7-ol]; JHS-198 [8-chloro-3-[6-(dimethylamino)hexyl]-2,3,4,5-tetrahydro-5-phenyl-1H-3-Benzazepin-7-ol in a 1:1 complex with cyanoborane]; JHS-136 [8-chloro-3-[4-(dimethylamino)butyl]-2,3,4,5-tetrahydro-5-phenyl-1H-3-Benzazepine-7-ol]; and NNC-22-0010 [S(+)-8-chloro-5-(5-bromo-2,3-dihydrobenzofuran-7-yl)-7-hydroxy-3-methyl-2,3,4,5-tetrahydro-1H-3-Benzazepine]. The foregoing D1/D5 antagonists can be prepared by known methods, e.g., by the methods described in U.S. 5,302,716, WO 93/13073, WO 93/1702, WO 95/25102, and J. Med. Chem 38 (21) pp. 4284–93 (1995), the contents of which are incorporated herein by reference. SCH 39166 and SCH 23390 are particularly preferred, with SCH 39166 being most preferred.

It will be appreciated by those skilled in the art that the doses effective for treating obsessive-compulsive disorder, somatoform disorders, dissociative disorders, eating disorders, impulse control disorders, and autism will vary depending on the particular individual treated, and the relative severity of the disorder. The D1/D5 antagonists are preferably administered at daily doses of 0.01 to 500 mg/kg of bodyweight, more preferably 0.01 to 150 mg/kg, most preferably 0.01 to 10 mg/kg. The daily dose may be administered in a single dose, or divided equally into several doses.

For preparing pharmaceutical compositions with the D1/D5 antagonists used in this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The D1/D5 antagonists may also be deliverable transdermally. The transdermal compositions can take the form of creams, lotions, aerosols and/or emulsions and can be included in a transdermal patch of the matrix or reservoir type as are conventional in the art for this purpose.

Preferably, the D1/D5 antagonists are administered orally.

EXAMPLE 1

Prepare pharmaceutical compositions containing SCH 39166 as the active ingredient:

| No. | Ingredient | mg/capsule | mg/capsule |
|---|---|---|---|
| 1. | SCH 39166 | 5.0 | 25.0 |
| 2. | Lactose USP | 114.0 | 94.0 |
| 3. | Sodium Starch Glycolate NF | 6.0 | 6.0 |
| 4. | Povidone USP (K29/32) | 4.0 | 4.0 |

-continued

| No. | Ingredient | mg/capsule | mg/capsule |
|---|---|---|---|
| 5. | Magesium Stearate NF | 1.0 | 1.0 |
|  | TOTAL | 130.0 mg | 130.0 mg |

Mix items 1–4 in a suitable blender for 10–15 minutes. Add item 5 and mix for 1–3 minutes. Fill the mixture into suitable two-piece hard gelatin capsules with a suitable encapsulating machine.

EXAMPLE 2

Administer the capsules of Example 1 (containing 5.0 mg of SCH 39166), once a day, for six months, to a patient diagnosed with obsessive-compulsive disorder, thereby reducing or eliminating the observable symptoms of the disorder.

EXAMPLE 3

Administer the capsules of Example 1 (containing 25.0 mg of SCH 39166) once a day, for six months to a patient diagnosed as having autism, thereby reducing or eliminating the observable symptoms of the disorder.

While the present invention has been described in conjunction with specific embodiments set forth above, many alternatives, modifications and variations thereof will be apparent to those of ordinary skill in the art. All such alternatives, modifications, and variations are intended to fall within the spirit and scope of the present invention.

What is claimed is:

1. A method for treating a human afflicted with a disorder selected from the group consisting of obsessive-compulsive disorder, somatoform disorders, dissociative disorders, eating disorders, impulse control disorders, and autism, said method comprising administering an effective amount of a D1/D5 antagonist wherein the D1/D5 antagonist is (−)-trans-6,7,7a,8,9,13b-hexahydro-3-chloro-2-hydroxy-N-methyl-5-H-benzo[d]naphtho{2,1-b}azepine HCl.

2. The method of claim 1, wherein the D1/D5 antagonist is administered at a daily dose of 0.01 to 500 mg/kg.

3. The method of claim 2, wherein the D 1/D5 antagonist is administered at a daily dose of 0.01 to 150 mg/kg.

4. The method of claim 3, wherein the D1/D5 antagonist is administered at a daily dose of 0.01 to 10 mg/kg.

5. The method of claim 1, wherein the disorder is obsessive-compulsive disorder.

6. The method of claim 1, wherein the disorders are selected from the group consisting of anorexia nervosa, bulimia, and binge eating.

7. The method of claim 1, wherein the disorder is autism.

8. The method of claim 1, wherein the disorder is an impulse control disorder from the group consisting of pathological gambling, compulsive buying, and sexual compulsion.

* * * * *